(12) United States Patent
Simpson et al.

(10) Patent No.: US 7,652,760 B1
(45) Date of Patent: Jan. 26, 2010

(54) SYSTEM FOR DETECTING COATINGS ON TRANSPARENT OR SEMI-TRANSPARENT MATERIALS

(75) Inventors: Jeffrey A. Simpson, Wayne, NE (US); Mark A. Imbrock, Sylvania, OH (US); Nathan Strimpel, Carleton, MI (US)

(73) Assignee: Electronic Design To Market, Inc., Toledo, OH (US)

(*) Notice: Subject to any disclaimer, the term of this patent is extended or adjusted under 35 U.S.C. 154(b) by 367 days.

(21) Appl. No.: 11/731,740

(22) Filed: Mar. 30, 2007

Related U.S. Application Data

(60) Provisional application No. 60/789,829, filed on Apr. 5, 2006.

(51) Int. Cl.
*G01N 21/00* (2006.01)

(52) U.S. Cl. ............ 356/239.1; 356/237.1; 356/73

(58) Field of Classification Search .......... None
See application file for complete search history.

(56) References Cited

U.S. PATENT DOCUMENTS

| | | |
|---|---|---|
| 1,503,543 A | 8/1924 | Lytle |
| 1,756,785 A | 4/1930 | Gallasch |
| 3,016,464 A | 1/1962 | Bailey |
| 3,137,756 A | 6/1964 | Günther et al. |
| 3,693,025 A | 9/1972 | Brunton |
| 3,807,870 A | 4/1974 | Kalman |
| 3,994,586 A | 11/1976 | Sharkins et al. |
| 4,207,467 A | 6/1980 | Doyle |
| 4,284,356 A | 8/1981 | Heilman |
| 4,848,913 A | 7/1989 | Greiner |
| 4,899,055 A | 2/1990 | Adams |
| 4,902,902 A | 2/1990 | Tole |
| 4,984,894 A | 1/1991 | Kondo |
| 5,054,927 A | 10/1991 | Garves |
| 5,132,631 A | 7/1992 | Klopfenstein et al. |
| 5,237,392 A | 8/1993 | Hickel et al. |
| 5,239,488 A | 8/1993 | Markham et al. |
| 5,254,149 A | 10/1993 | Hashemi et al. |
| 5,442,573 A | 8/1995 | Bredberg et al. |
| 5,490,728 A | 2/1996 | Schietinger et al. |
| 5,525,138 A | 6/1996 | Hashemi et al. |
| 5,564,830 A | 10/1996 | Bobel et al. |
| 5,568,264 A | 10/1996 | Nakatsuka et al. |
| 5,581,355 A | 12/1996 | Myers et al. |
| 5,597,237 A | 1/1997 | Stein |
| 5,637,873 A | 6/1997 | Davis et al. |
| 5,657,124 A | 8/1997 | Zhang et al. |
| 5,726,749 A | 3/1998 | Schave |
| 5,726,756 A | 3/1998 | Aki et al. |
| 5,727,017 A | 3/1998 | Maurer et al. |

(Continued)

FOREIGN PATENT DOCUMENTS

| | | |
|---|---|---|
| CA | 2539676 A1 | 9/2006 |
| DE | 22584 | 1/1962 |
| EP | 0480027 A | 4/1992 |
| GB | 2321309 B | 8/1999 |
| JP | 53-16652 A | 2/1978 |

(Continued)

*Primary Examiner*—Gregory J Toatley, Jr.
*Assistant Examiner*—Amanda H Merlino
(74) *Attorney, Agent, or Firm*—MacMillan, Sobanski & Todd, LLC

(57) ABSTRACT

A system for detecting coatings on a transparent or semi-transparent medium includes a conductive sensor and a light reflection sensor which are configured to determine a presence and the conductivity of the coating on the medium.

20 Claims, 1 Drawing Sheet

U.S. PATENT DOCUMENTS

| | | |
|---|---|---|
| 5,748,091 A | 5/1998 | Kim |
| 5,838,446 A | 11/1998 | Meth et al. |
| 5,966,214 A | 10/1999 | Imbrock et al. |
| 6,683,695 B1 | 1/2004 | Simpson et al. |
| 7,061,612 B2 | 6/2006 | Johnston |
| 2006/0054843 A1 | 3/2006 | Simpson et al. |
| 2006/0209304 A1 | 9/2006 | Simpson et al. |

FOREIGN PATENT DOCUMENTS

| | | |
|---|---|---|
| JP | 56-44804 A | 4/1981 |
| JP | 60-147606 A | 8/1985 |
| SU | 1585670 A | 8/1990 |
| WO | WO 99/58928 A1 | 11/1999 |
| WO | WO 01/07882 A1 | 2/2001 |

SYSTEM FOR DETECTING COATINGS ON TRANSPARENT OR SEMI-TRANSPARENT MATERIALS

CROSS-REFERENCE TO RELATED APPLICATION

The present invention claims the benefit of the provisional patent application Ser. No. 60/789,829 filed Apr. 5, 2006.

BACKGROUND OF THE INVENTION

The manufacturing industries have developed several types of coatings for glass and other types of transparent and semi-transparent materials. It is also important that the location of any coated surface is known during the manufacturing process. It is especially important that there be a method to distinguish the non-conductive coatings from any type of conductive coatings.

For example, in the coating and glass industry, for example, there are numerous applications where residual coatings from the manufacturing process or spectral reflective coatings are applied to a transparent surface. In particular, for architectural applications, surface coatings are often used on glass to reduce thermal transfer through the glass. The coatings are effective for reflecting and/or absorbing certain wavelengths of solar radiation that strike it. The coatings are generally in the form of an electrically conductive transparent film on one surface of the glass. It is often difficult to visually detect the presence or absence of a solar surface coating on glass.

Further, even when the presence of a solar coating is detected, it is almost impossible to visually detect which side of the glass sheet is coated. It may be desirable to have the coated surface on the interior of the building to protect the coating from the outside environment. The problem may become even more important where a window pane assembly is formed from two spaced sheets of glass. Preferably, a solar coating is placed on the interior surface, i.e., the surface between the two panes, of the outer glass pane. If the coating is located on the inner glass pane, there may be excessive heat buildup between the spaced window panes which could lead to premature failure of the seal between the panes.

Currently, one method for detecting a non-conductive coating uses an optical reflection method where light is emitted onto and reflected from the coated surface. The amount of light energy reflected from a non-conductive coated surface is different from a clear or uncoated surface. However, there is a need to improve this reflection method since there is a vast proliferation of new types of non-conductive coatings. Many of the new non-conductive coating have the same reflection characteristics when exposed to light from a limited spectrum light source (i.e., monochrome light source, Laser, LED, etc.) as the reflection characteristics of conductive LOW E (Low Emissivity) coatings. This inability to easily determine the presence and location (i.e., on which side of glass is which coating) causes a concern since LOW E coating must be on the inside of a sealed window, while many non-conductive coatings are designed for the outside surface of a sealed window assembly. It is thus important that those installing the glass install the glass in the proper orientation.

While there is a currently used method for detecting a conductive coating using a capacitance method, such method does not reliably detect the surface location of the conductive coating and cannot detect the presence or location of non-conductive coatings.

Further, another detection method involves a continuity test device in which a device must touch the coating on the medium. However, this device can damage the coating which is unacceptable.

Therefore, there is a continuing need for an improved, reliable and efficient method and device to detect the presence, location and type of coating applied to various transparent or semi-transparent mediums, or materials deposited directly to the surface or left on the transparent mediums.

BRIEF SUMMARY OF THE INVENTION

This invention relates to a system for detecting coatings on a transparent or semi-transparent medium. The system includes a conductive sensor and a light reflection sensor which are configured to determine the coating location and conductivity of a coating on the medium. In certain embodiments, the detection system is configured to determine the conductivity when either in direct contact with the medium or not in contact with the medium.

In another aspect, the present invention relates to a method for detecting coatings on a transparent or semi-transparent medium which includes providing a conductive sensor and a light reflection sensor which are configured to determine the coating location, conductivity, types of coatings, and analytical value(s) of the coatings.

Various objects and advantages of this invention will become apparent to those skilled in the art from the following detailed description of the preferred embodiment, when read in light of the accompanying drawings.

DETAILED DESCRIPTION OF THE INVENTION

Figure 1:
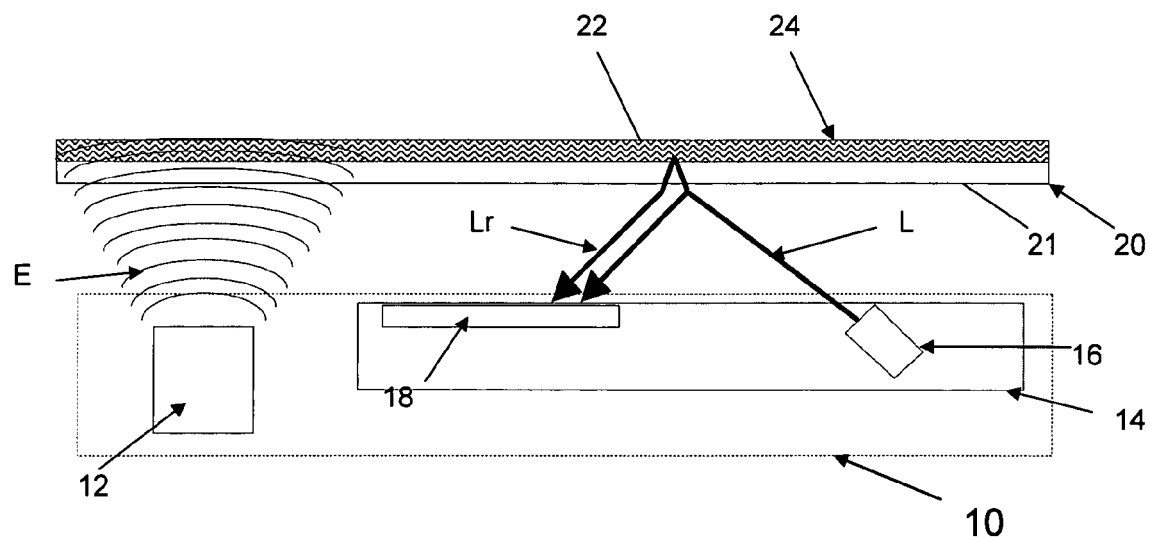
FIG. 1 is a schematic illustration of a system for detecting a coating on a transparent or semi-transparent medium.

The invention relates generally to a system 10 for the detection of a coating on a transparent or semi-transparent medium 20, as generally shown in FIG. 1. The transparent or semi-transparent medium 20 can be comprised of a glass and/or plastic materials.

In one non-limiting embodiment, the transparent or semi-transparent medium 20 can be a single sheet of glass that may have one or both sides coated with a transparent or semi-transparent material.

In another non-limiting embodiment, the transparent or semi-transparent medium 20 can be at least one or more of a single pane window assembly, a dual pane window assembly and a triple pane window assembly. Such window assemblies may have one or more panes coated with a transparent or semi-transparent material. It is to be thus understood that the present system is useful with many types of transparent or semi-transparent media, and that for ease of discussion herein, such media will generally be referred to as the medium 20.

The medium 20 has a first surface 21 and a second surface 22. In the schematic illustration in FIG. 1, the medium 20 is depicted as having a coating 24 in order to aid in the explanation of the invention herein.

The detection system 10 can: i) determine whether the coating 24 is present, and can ii) further distinguish whether the coating is a conductive coating or a non-conductive coating. In one particular embodiment, the detection system 10 is especially useful to determine the presence of self-clean coatings on glass.

The detection system 10 includes a conductive sensor 12 and a light reflection sensor 14. Together, the conductive sensor 12 and the light reflection sensor 14 are used together to detect and confirm the presence and location of a conductive or non-conductive coating 24 on the transparent or semi-transparent medium 20. It is to be understood that the detection system 10 can be configured such that the conductive sensor 12 and the light reflection sensor 14 are operated substantially simultaneously, or are operated in a sequential manner.

The conductive sensor 12 confirms the absence of a conductive coating 24. The conductive sensor 12 directs an electric field E toward the medium 20, and depending on the signals detected, determines whether the coating 24 is made of a conductive material. In one embodiment, the conductive sensor 12 is a non-contact and/or contact inductive sensor. In another embodiment, the conductive sensor 12 is a non-contact and/or contact capacitive sensor. In both embodiments, the conductive sensor 12 is thus used to confirm whether the coating 24 is a conductive or non-conductive material.

In one embodiment, the conductive sensor 12 can be a non-contact capacitive sensor, although other suitable conductive sensors may be used. It should be noted that the detection system 10 is useful to determine the presence and location of any non-conductive coatings that have different reflection characteristic than from a surface that is clear of any coatings (uncoated).

The light reflection sensor 14 confirms the presence and location of any coating 24. The light reflection sensor 14 includes a light source 16 and one or more light sensing elements 18. The light source 16 directs light L toward the medium 20. The light L comprises any light having a desired wavelength which can be modified, depending on end-use requirements.

Reflected light energy $L_r$ from the medium 20 is used to determine whether the coating 24 is present. If the coating 24 is present, the angle of the reflected light and the receiving of energy $L_r$ indicates the location of the coating 24.

One suitable light source 16 can be used herein will be referred to as an IR (Infrared) laser although other suitable light sources may be used. In one such embodiment, the reflection from the IR laser light source 16 is measured on line or area sensor elements 18. The light sensor elements 18 are able to determine reflected energy from multiple reflecting surfaces (i.e., the first surface 21 and second surface 22 from a single pane of glass; and, first, second, third and fourth surfaces for a dual pane assembly with similar results for triple pane assemblies). The measured reflected energy from each surface 21 and 22 determines the presence and location of the coating 24. The resulting measured reflected energy is then correlated with the conductive sensor 12 to determine if the coating is a conductive LOW E coating or a non-conductive self-clean coating. Since LOW E coatings are conductive, if the LOW E coating is present, the conductive sensor 12 will detect it. The conductive sensor 12 cannot detect a non-conductive coating. Therefore, the results from the conductive sensor 12 are used in correlation with the reflection sensor 14. The reflection characteristics of the IR laser 16 resulting from the glass surfaces are analyzed for each surface and compared to the refection characteristics of clear glass to determine the presence and location of the coating.

The detection system 10 thus uses the conductive sensor 12 in correlation with the light reflection sensor 14 to determine coating location(s), conductivity, type(s) of coatings, and analytical value(s). For example, the peak values, intensity and weightings of each sensing element in the sensor elements 18 can be determined. Other measurements from the reflection data: slope relationship of multiple frequency light sources; the absolute value of the reflected signals due to different surfaces of the medium under test; the ratio of reflected energy from each surface of the medium under test; and/or the absolute power amounts of multiple surface reflections.

In certain embodiments, the detection system 10 can either include or be in communication with a computer system configured to analyze results generated by the light reflection sensor and the conductive sensor. In certain embodiments, the values may be taught to a microcomputer by testing samples of the different coatings and of different surface coating locations for various samples of glass or other transparent material and for various commercial composites. The presence, location and/or type of a coating are determined by comparing the surface reflection energy levels with the stored information for the different samples.

This device may include an array of LED indicators which are selectively illuminated to indicate the presence of a reflective surface coating and the surface location of the reflective coating. Alternately, other types of indicators may be provided. For example, a reflected energy magnitude signal may be provided for manually comparing with a table of different reflected energy magnitudes for coatings on the different surfaces of standard glass. By comparing the indicated magnitude with the readings for the particular type of glass being measured, the presence and surface location of any coating will be readily apparent. These indicators also may provide information on the thickness of the material and the spacing of sheets forming a composite.

In certain embodiments, the detection system 10 can be used to distinguish between types of coatings and/or differentiate between different manufacturers of the coatings, based at least in part on the amount of reflection from the coating 24.

The detection system 10 can be used in a contact or in a non-contact method of operation. Thus, the conductive sensor 12 may be a non-contact and/or contact capacitive sensor. In another embodiment, the conductive sensor 12 may be a non-contact and/or contact inductive sensor.

Also, the light reflection sensor 14 can use any light source and wavelength. Further, the reflection sensor 14 can use one or multiple light sources. Also, the reflection sensor 14 can use one or more optical sensors. In certain embodiments, the detection system 10 may include a plurality of conductive sensors 12 and reflection sensors 14.

Figure 2:
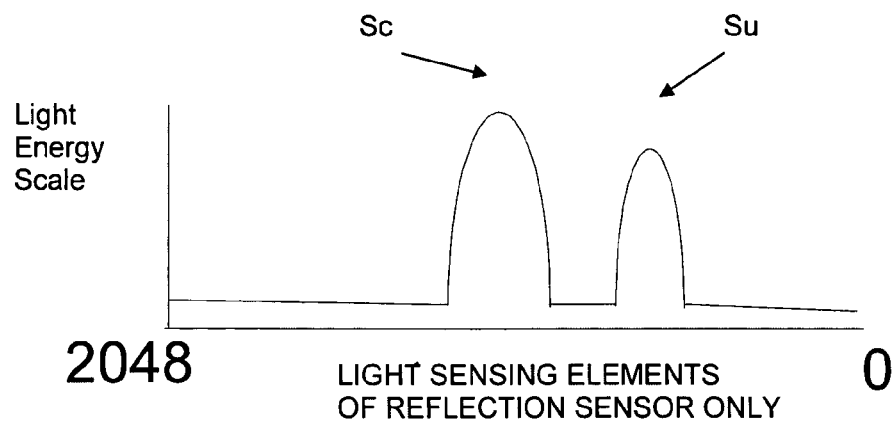
FIG. 2 is a graph of a light energy scale showing that the amount of light energy reflected from a non-conductive coated surface (Sc) is different from a clear or uncoated surface (Su).

FIG. 2 is a graph of a light energy scale showing that the amount of light energy reflected from a non-conductive coated surface is different from a clear glass (uncoated) surface. The coated surface $S_c$ shows the effect of reflected energy from the second, or coated, surface 22. The uncoated, or clear, surface $S_u$ shows the effect of reflected energy from the first surface 21.

It is to be understood that various suitable algorithms or mathematical techniques can be used with the present invention. Further, the detection system 10 may be controlled and/or operated by conventional control and/or operational systems, including, but not limited to various software instructions and/or programs. It is to be understood that such instructions and programs are readily available to, or readily programmable, without undue experimentation from the descriptions as provided herein.

While the invention has been described with reference to a preferred embodiment, it should be understood by those skilled in the art that various changes may be made and equivalents may be substituted for elements thereof without departing from the essential scope of the invention. In addition, many modifications may be made to adapt a particular situation to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims.

We claim:

1. A system for detecting coatings on at least one transparent or semi-transparent medium, comprising:
   at least one conductive sensor for detecting a conductive coating without being in contact with the medium,
   the conductive sensor being configured: to direct an electric field E toward the medium, and depending on whether a signal is detected, to determine whether the coating is made of a conductive material; and
   at least one light reflection sensor for detecting: i) a non-conductive coating and, ii) a location of one or more coatings on one or more surfaces of the medium,
   the light reflection sensor being configured: to provide reflection energy magnitude characteristics resulting from one or more surfaces of the medium;
   the reflection energy magnitude characteristics being compared to reflection characteristics of at least one of: clear glass, transparent material and composite materials;
   the conductive sensor and the reflection sensor configured to determine a presence of a coating, and if present, determining: the coating location, the coating conductivity, and the type of coating.

2. The detection system of claim 1, wherein the conductive sensor is configured to determine the conductivity when in direct contact with the medium.

3. The detection system of claim 1, wherein the conductive sensor is configured to determine the conductivity when not in direct contact with the medium.

4. The detection system of claim 1, wherein the conductive sensor is a capacitive sensor.

5. The detection system of claim 1, wherein the conductive sensor is an inductive sensor.

6. The detection system of claim 1, wherein the light reflection sensor comprises one or more light sources, each having a desired wavelength.

7. The detection system of claim 1, wherein the light reflection sensor comprises one or more optical sensors.

8. The detection system of claim 1, further including a computer system configured to analyze results generated by the light reflection sensor and the conductive sensor.

9. The detection system of claim 1, wherein at least one conductive sensor and at least one light reflection sensor are configured to substantially simultaneously determine the presence and conductivity of any coating on the medium.

10. The detection system of claim 1, wherein the transparent or semi-transparent medium comprises at least one or more of a single pane window assembly, a dual pane window assembly, and a triple pane window assembly.

11. A method for detecting coatings on a transparent or semi-transparent medium, comprising:
   i) directing a light toward the medium and receiving reflected light from the medium;
   ii) comparing reflection characteristics resulting from one or more surfaces of the medium to reflection characteristics of at least one of: clear glass, transparent material and composite materials, to determine the presence and location of the coating;
   iii) determining the presence or absence of a conductive coating on at least one surface of the medium by directing an electric field toward the medium, and if any conductive coating is present,
   iv) determining one or more of: the coating location, the coating conductivity, the type of coating, and one or more analytical values of the medium.

12. The method of claim 11, including determining the conductivity of the coating by directly contacting the medium with the electric field.

13. The method of claim 11, including determining the conductivity of the coating by not directly contacting the medium with the electric field.

14. The method of claim 11, including using a capacitive sensor in step iii).

15. The method of claim 11, including using an inductive sensor in step iii).

16. The method of claim 11, including using a light sensor in step iii), wherein the light reflection sensor comprises one or more light sources, each having a desired wavelength.

17. The method of claim 11, including using a light sensor in step iii), wherein the light reflection sensor comprises one or more optical sensors.

18. The method of claim 11, further including a computer system configured to analyze results generated by a light reflection sensor and a conductive sensor.

19. The method of claim 11, wherein at least one conductive sensor and at least one light reflection sensor are configured to substantially simultaneously determine the presence and conductivity of any coating on the medium.

20. The method of claim 11, wherein the transparent or semi-transparent medium comprises at least one or more panes or surfaces of a window assembly or film or applied film assembly.

* * * * *